(12) United States Patent
Lehn et al.

(10) Patent No.: US 7,981,436 B2
(45) Date of Patent: Jul. 19, 2011

(54) HYDROGELS FOR THE CONTROLLED RELEASE OF BIOACTIVE MATERIALS

(75) Inventors: Jean-Marie Lehn, Strasbourg (FR); Nampally Sreenivasachary, Strasbourg (FR); Andreas Herrmann, Veyrier (CH)

(73) Assignees: Firmenich SA, Geneva (CH); Universite Louis Pasteur, Strasbourg (FR); Centre National de la Recherche Scientifique, Paris Cedex (FR)

( * ) Notice: Subject to any disclaimer, the term of this patent is extended or adjusted under 35 U.S.C. 154(b) by 985 days.

(21) Appl. No.: 11/851,106

(22) Filed: Sep. 6, 2007

(65) Prior Publication Data
US 2008/0057005 A1    Mar. 6, 2008

Related U.S. Application Data

(63) Continuation of application No. PCT/IB2006/050876, filed on Mar. 22, 2006.

(30) Foreign Application Priority Data

Mar. 24, 2005  (WO) ............... PCT/IB2005/000815

(51) Int. Cl.
*A61K 8/30*     (2006.01)
*A61K 31/4985*  (2006.01)
*A61K 31/52*    (2006.01)
*A61L 9/04*     (2006.01)

(52) U.S. Cl. ......... 424/405; 424/49; 424/70.1; 510/101; 510/103; 510/104; 512/4; 514/252.1; 514/263.37

(58) Field of Classification Search .................. None
See application file for complete search history.

(56) References Cited

FOREIGN PATENT DOCUMENTS
WO    WO 01/51689 A1    7/2001

OTHER PUBLICATIONS

J. Sunamoto et al., XP008066012, "Synthesis of Folic Acid Moiety-Conjugated Hydrophobized Pullulan (FA-CHP) as a Carrier of Anticancer Drugs", Polymer Preprints, vol. 45, No. 2, pp. 440-441 (2004).
N. Sreenivasachary et al., XP008066044, "Gelation-Driven Component Selection In The Generation Of Constitutional Dynamic Hydrogels Based On Guanine-Quartet Formation", Proceedings Of The National Academy Of Sciences (PNAS), vol. 102, No. 17, pp. 5938-5943, (2005).
W. Guschlbauer et al., "Four-Stranded Nucleic Acid Structures 25 Years Later: From Guanosine Gels to Telomer DNA", Journal of Biomolecular Structure & Dynamics, ISSN 0739-1102, vol. 8, Issue No. 3 (1990).
J. Sunamoto et al., XP008066012, "Synthesis of Folic Acid Moiety-Conjugated Hydrophobized Pullulan (FA-CHP) as a Carrier of Anticancer Drugs", Polymer Preprints, vol. 45, No. 2, pp. 440-441 (2004).
N. Sreenivasachary et al., XP008066044, "Gelation-Driven Component Selection In The Generation of Constitutional Dynamic Hydrogels Based on Guanine-Quartet Formation", Proceedings Of The National Academy Of Sciences (PNAS), vol. 102, No. 17, pp. 5938-5943, (2005).
W. Guschlbauer et al., "Four-Stranded Nucleic Acid Structures 25 Years Later: From Guanosine Gels to Telomer DNA", Journal of Biomolecular Structure & Dynamics, ISSN 0739-1102, vol. 8, Issue No. 3 (1990).
International Search Report and Written Opinion, PCT/IB06/50876, mailed Jul. 20, 2006.

*Primary Examiner* — Sharmila G. Landau
*Assistant Examiner* — Kyle Purdy
(74) *Attorney, Agent, or Firm* — Winston & Strawn LLP

(57) ABSTRACT

The present invention relates to the formation of hydrogels based on guanosine hydrazide derivatives in the presence of cations. The hydrogels can be used as a carrier/delivery system for biologically active substances such as flavors, fragrances, insect attractants or repellents, bactericides, fungicides, pharmaceuticals or agrochemicals.

18 Claims, 2 Drawing Sheets

HYDROGELS FOR THE CONTROLLED RELEASE OF BIOACTIVE MATERIALS

CROSS-REFERENCE TO RELATED APPLICATION(S)

This application is a continuation of International application PCT/IB2006/050876 filed on Mar. 22, 2006, the entire content of which is expressly incorporated herein by reference thereto.

TECHNICAL FIELD

The present invention relates to the formation of stable supramolecular hydrogels based on guanosine hydrazide derivatives being able to associate through Hoogsten-type hydrogen-bonding to form supramolecular macrocycles in the presence of cations.

BACKGROUND

The stabilization and controlled delivery of bioactive molecules such as flavors, fragrances, pharmaceuticals or agrochemicals, is an important issue for nearly all applied sciences. Without the stabilization of a concentrated, easily transportable and processible form of the (bio)active agent delivery becomes unreliable and the functional agents will only rarely exhibit their beneficial properties at the predetermined place and time. Indeed, effective encapsulation is required in a wide range of applications, in order to protect sensitive additives from degradation and to control their release and hence optimize their performance according to the requirements of the application. The entrapping of active compounds into a matrix such as micelles, capsules or gels has widely been studied in various branches of industry.

The controlled release of flavors and fragrances, which are highly volatile and can thus only be perceived over a limited period of time, has recently attracted much interest from the flavor and fragrance industry. Active volatile material dispensers, such as air-fresheners, are consumer products commonly used in every day life, and several different types thereof are known. Gels attracted much interest for their potential in the release of flavors and/or fragrances.

Gels, in particular those formed from low molecular weight compounds that respond to pH, are also interesting for biomedical applications.

Non-functionalized guanosines are known to undergo quadruple association into G-quartets through Hoogsten-type hydrogen-bonding forming supramolecular macrocycles which stack into $G_4$-assemblies in the presence of cations such as $Na^+$, $K^+$, and $NH_4^+$ with formation of hydrogels (Guschlbauer et al., J. Biomol. Struct. Dyn., 1990, 8, 491-511). The structures are not known to interact with active substances.

SUMMARY OF THE INVENTION

The present invention relates to a new gel composition, consisting of a guanosine hydrazide derivative, in the presence of a cation and a water-based liquid. The hydrogel assemblies can interact with various active aldehydes or ketones and influence their release into the surrounding environment. The present invention concerns the hydrogels, their use to protect biologically active substances as well as their use as delivery systems for the controlled release of flavors, fragrances, pharmaceuticals or agrochemicals, as well as consumer products containing these gels. The gels of the invention are particularly useful in the field of perfumery and flavoring.

DETAILED DESCRIPTION OF THE PREFERRED EMBODIMENTS

Figure 1:
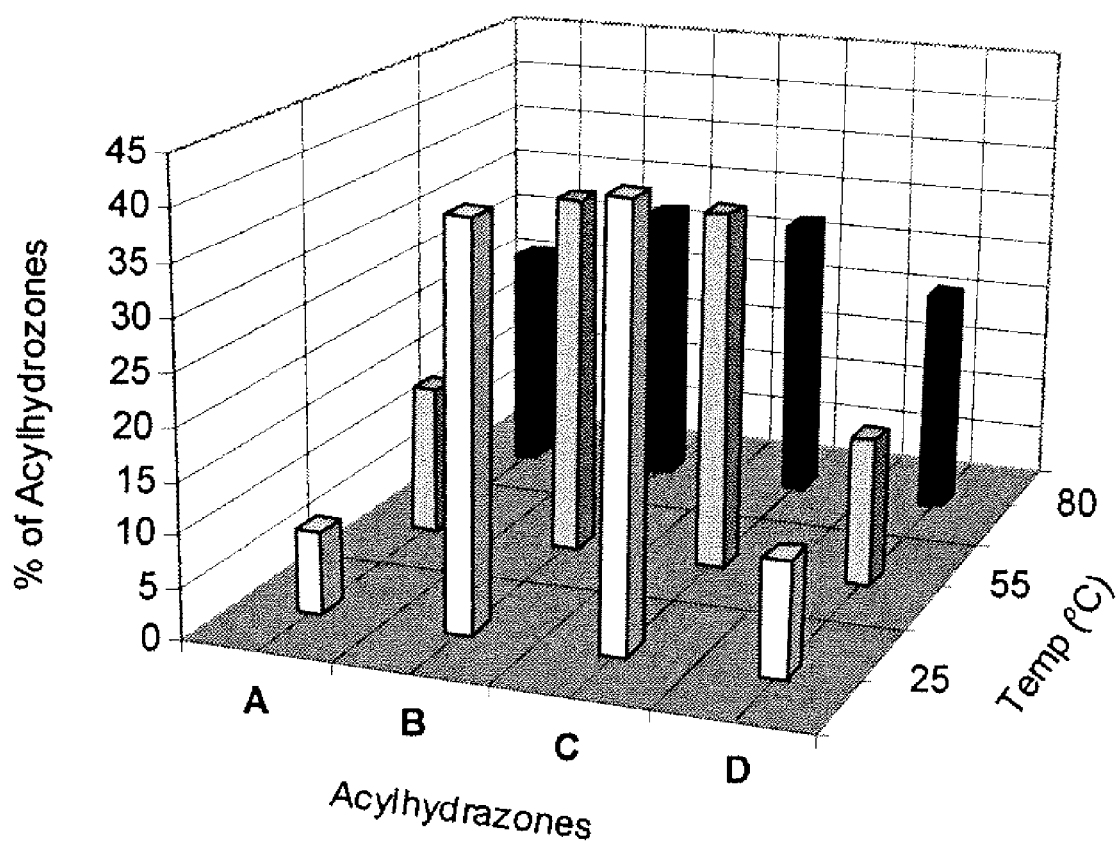
FIG. 1 represents the distribution of the acylhydrazones A-D of example 4 in the constitutional dynamic library generated from a mixture of the hydrazides 1, 2 and the aldehydes 3 and 4 of the same example as function of temperature after reaching equilibrium, as calculated from integration of the CH=N $^1$H-NMR signals.

The present invention relates to a new gel composition, consisting of a guanosine hydrazide derivative, a cation and a water-based liquid. The gel is a useful carrier for biologically active substances, such as aldehydes or ketones, which can be entrapped within the hydrogel and released to the surroundings during application.

Therefore, a further embodiment of the invention concerns an active gel obtainable by admixing together the above-mentioned gel and at least one biologically active substance. The release of these substances is then dependent on the strength of the interactions between the gel, or the gel components, and the active substances, as well as the diffusion of the substances out of the hydrogel.

By "active substance" it is meant here an ingredient capable of bringing a benefit or effect into its surrounding environment, and having in particular, a perfuming, flavoring, pharmaceutical, insect repellent or attractant, insecticide, antibacterial, agrochemical effect and mixtures thereof. By "active gel" it is meant here a gel capable of releasing at least one active substance.

Consequently, a first object of the present invention is a gel comprising:

1) at least one compound of formula

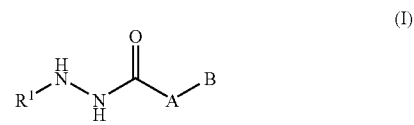

(I)

wherein $R^1$ represents a hydrogen atom, a $C_1$-$C_{10}$ linear or branched alkyl group or a phenyl group;

A is selected from the group consisting of formulae i) to vi),

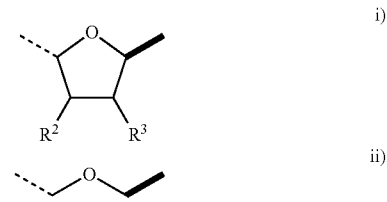

-continued

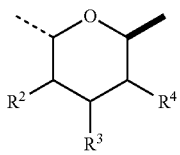
iii)

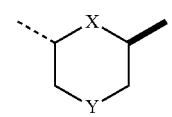
iv)

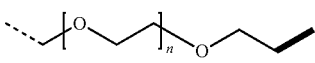
v)

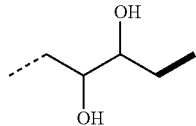
vi)

in which formulae the dotted and the bold lines indicate the connection to the —CONHNHR$^1$ and B moieties, respectively, and R$^2$, R$^3$ or R$^4$ are, independently from each others, selected from the group consisting of —H, —OH, —OCOCH$_3$, —OCH$_2$Ph, —OPO$_3$NaH, and —OPO$_3$H$_2$, or, taken two of them together, of —OP(OH)OO—, —OP(ONa)OO—, and —OC(CH$_3$)$_2$O—; and Y and X are a NH group or oxygen atom or a CH$_2$ or CHOH group; and n is an integer varying from 1 to 50, preferably from 1 to 10; and B is a moiety of formulae vii) to x)

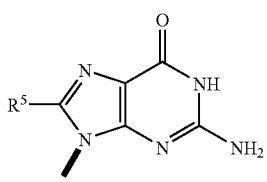
vii)

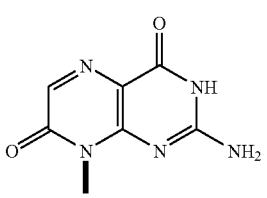
viii)

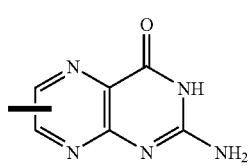
ix)

x)

in which formulae the bold line indicates the connection to the A moiety, and R$^5$ is selected from the group consisting of —H, —OH, —OCH$_3$, —SH, —SCH$_3$, —NH$_2$, —NHCH$_3$, —OCOCH$_3$, —OCH$_2$Ph, —OCH$_2$CH=CH$_2$, and —Br;

2) a salt comprising at least one cation selected from the group consisting of K$^+$, Na$^+$, Li$^+$, Rb$^+$, Cs$^+$, Sr$^{2+}$, Ba2+, NH$_4^+$ or (CH$_3$)$_4$N+, and at least one anion selected from the group consisting of Cl$^-$, Br$^-$, I$^-$, NO$_3^-$, HCOO$^-$, CH$_3$COO$^-$, H$_2$PO$_3^-$, HPO$_3^{2-}$, PO$_3^{3-}$, SO$_4^{2-}$, CO$_3^{2-}$, HCO$_3^-$, BO$_2^-$, PF$_6^-$, picrate$^-$ and citrate$^{3-}$; and 3) a water-based liquid.

Preferred compounds of formula (I) are those wherein A is selected from formulae i) or ii), with R$^2$ and R$^3$ being independently of each others —H or —OH, B is a moiety of formula vii) or x) and R$^1$ and R$^5$ represent hydrogen atoms.

More preferred compounds of formula (I) are those of formula

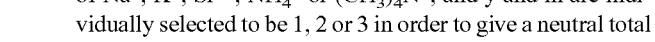
(II)

wherein R$^2$ and R$^3$ are independently of each others —H or —OH, which are also an object of the present invention.

Even more preferred is guanosine-5'-hydrazide.

Preferred salts are of formula M$_y$X$_m$, wherein X is an anion selected from the group consisting of Cl$^-$, NO$_3^-$, HCOO$^-$, CH$_3$COO$^-$, HCO$_3^-$, H$_2$PO$_3^-$, HPO$_3^-$, SO$_4^{2-}$, CO$_3^{2-}$, PO$_3^{3-}$ and citrate$^{3-}$, M is a cation selected from the group consisting of Na$^+$, K$^+$, Sr$^{2+}$, NH$_4^+$ or (CH$_3$)$_4$N$^+$, and y and m are individually selected to be 1, 2 or 3 in order to give a neutral total charge for the salts of formula M$_y$X$_m$.

More preferably M is K$^+$, Na$^+$ or N(CH$_3$)$_4^+$. More preferably X is Cl$^-$, CH$_3$COO$^-$, H$_2$PO$_3^-$, HPO$_3^{2-}$, PO$_3^{3-}$, SO$_4^{2-}$, or citrate$^{3-}$.

Preferred water-based liquids are water and homogeneous mixtures of water with ethanol, dipropylene glycol or propylene glycol. According to a particular embodiment of the invention, the water-based liquid has a pH comprised between 5 and 8, and the pH may be held constant by a buffer.

According to a further embodiment of the invention the water-based liquids may further comprises a co-solvent selected from the group of the compounds known under the tradename Isopar® H, J, K, L, M, P or V (isoparaffins; origin: Exxon Chemical), Norpar® 12 or 15 (paraffins; origin: Exxon Chemical), Exxsol® D 155/170, D 40, D 180/200, D 60, D 70, D 80, D 100, D 110 or D 120 (dearomatized hydrocarbons; origin: Exxon Chemical), Dowanol® PM, DPM, TPM, PnB, DPnB, TPnB, PnP or DPnP (glycol ethers; origin: Dow Chemical Company), Eastman® EP, EB, EEH, DM, DE, DP or DB (glycol ethers; origin: Eastman Chemical Company), Dowanol® PMA or PGDA (glycol ether esters; origin: Dow Chemical Company) or Eastman® EB acetate, Eastman® DE acetate, Eastman® DB acetate, Eastman® EEP (all glycol ether esters; all origin: Eastman Chemical Company), or other solvents such as ethanol, dipropylene glycol, propylene glycol, ethylene glycol ethyl ether acetate, ethylene glycol diacetate, isopropyl myristate, diethyl phthalate, 2-ethylhexyl acetate, methyl n-amyl ketone or di-isobutyl ketone or also methanol, DMSO, dioxane, butanol, tert-butanol, propanol and isopropanol.

The invention's gel is formed with the best yields at neutral or slightly acidic pH. The concentration of the compound of formula (I), in the water-based liquid can be varied between 1 and 1000 mM, preferably between 10 and 200 mM, more preferably between 10 and 80 mM. The concentration of the salt required for the formation of the gel is preferably higher than 10 mM, more preferably higher than 30 mM and even more preferably higher than 45 mM, but in general not exceeding 2000 mM. The concentration of the compound of formula (I), as well as that of the salt influences the temperature of gelation and a person skilled in the art may want to choose these concentrations in order to obtain a particular gelation temperature suitable for the targeted application.

The gel according to the invention can also comprise, as optional components, at least one of the ingredients selected from the group consisting of antioxidants, UV-inhibitors, oil soluble dyes, solvents, surfactants and bittering agents.

As non-limiting examples of useful antioxidant components, one can cite the sterically hindered amines, i.e. the derivatives of the 2,2,6,6-tetramethyl-piperidine, such as those known under the tradename Uvinul® (origin: BASF AG) or Tinuvin® (origin: Ciba Speciality Chemicals), as well as the alkylated hydroxyarene derivatives, such as butylated hydroxytoluene (BHT).

The antioxidant component may be incorporated in the composition according to the invention in an amount comprised between 0% and 3%, the percentages being relative to the total weight of the composition. Preferably, the antioxidant component is present in amounts comprised between 0.1% and 2%.

As non-limiting examples of useful UV-inhibitor components, one can cite benzophenones, diphenylacrylates or cinnamates such as those available under the trade name Uvinul® (origin: BASF AG).

The UV-inhibitor component may be incorporated in the composition according to the invention in an amount comprised between 0% and 0.5%, the percentages being relative to the total weight of the composition. Preferably, the UV-inhibitor component is present in amounts comprised between 0.01% and 0.4%.

Dyes are another optional components of the invention composition. Suitable dyes are oil-soluble. Non-limiting examples of suitable dyes are derivatives of the anthraquinone, methines, azo, triarylmethane, triphenylmethane, azine, aminoketone, spirooaxine, thioxanthane, phtalocyanine, perylene, benzopyran or perinone families. Example of such dyes which are commercially available are known under the tradename Sandoplast® Violet RSB, Violet FBL, Green GSB Blue 2B or Savinyl® Blue RS (all anthraquinone derivatives, origin: Clariant Huningue S.A.), Oilsol® Blue DB (anthraquinone; origin: Morton International Ltd.), Sandoplastφ Yellow 3G (methine, origin: Clariant Huningue S.A.), Savinyl® Scarlet RLS (azo metal complex origin: Clariant Huningue S.A.), Oilsol® Yellow SEG (monoazo; origin: Morton International Ltd.), Fat Orange® R (monoazo; origin: Hoechst AG), Fat Red® 5B (diazo; origin: Hoechst AG), Neozapon® Blue 807 (phtalocyanine; origin: BASF AG), Fluorol® Green Golden (perylene; origin: BASF AG).

The dye component may be incorporated into the composition according to the invention in an amount comprised between 0% and 1%, the percentages being relative to the total weight of the composition. Preferably, the dye component is present in amounts comprised between 0.005% and 0.5%.

Surfactans may be cationic, anionic or non-ionic and can be present in an amount varying between 0.1 and 15%, preferably between 1 and 10%, more preferably between 1 and 5%.

The presence of a bittering agent may be desirable in order to render the product unpalatable, making it less likely that the composition is ingested, especially by young children. One can cite, as non-limiting example, isopropyl alcohol, methyl ethyl ketone, methyl n-butyl ketone or yet a denatonium salt such as the denatonium benzoate known also under the trademark Bitrex™ (origin: Mac Farlan Smith Ltd.).

The bittering component may be incorporated into the composition according to the invention in an amount comprised between 0% and 6%, the percentages being relative to the total weight of the composition. In the case of Bitrex® the maximum amount can be lowered to up to 0.1% of the total weight of the composition.

Preferably, the bittering component is present in amounts comprised between 0.5% and 5%. In the case of Bitrex® these amounts can be comprised between 0.001% to 0.05% of the total weight of the composition.

It is believed that the compound of formula (I), in the presence of cations M such as $K^+$, $Na^+$, $Sr^{2+}$, $N(CH_3)_{4+}$ and $NH_{4+}$, undergo association through Hoogsten-type hydrogen-bonding forming supramolecular macrocycles which stack with formation of hydrogels. An example of such association is illustrated in Scheme 1, wherein the compounds of formula (I) undergo quadruple association into G-quartets.

Scheme 1: Self assembly of the hydrogelator to G-quartets in presence of cations.

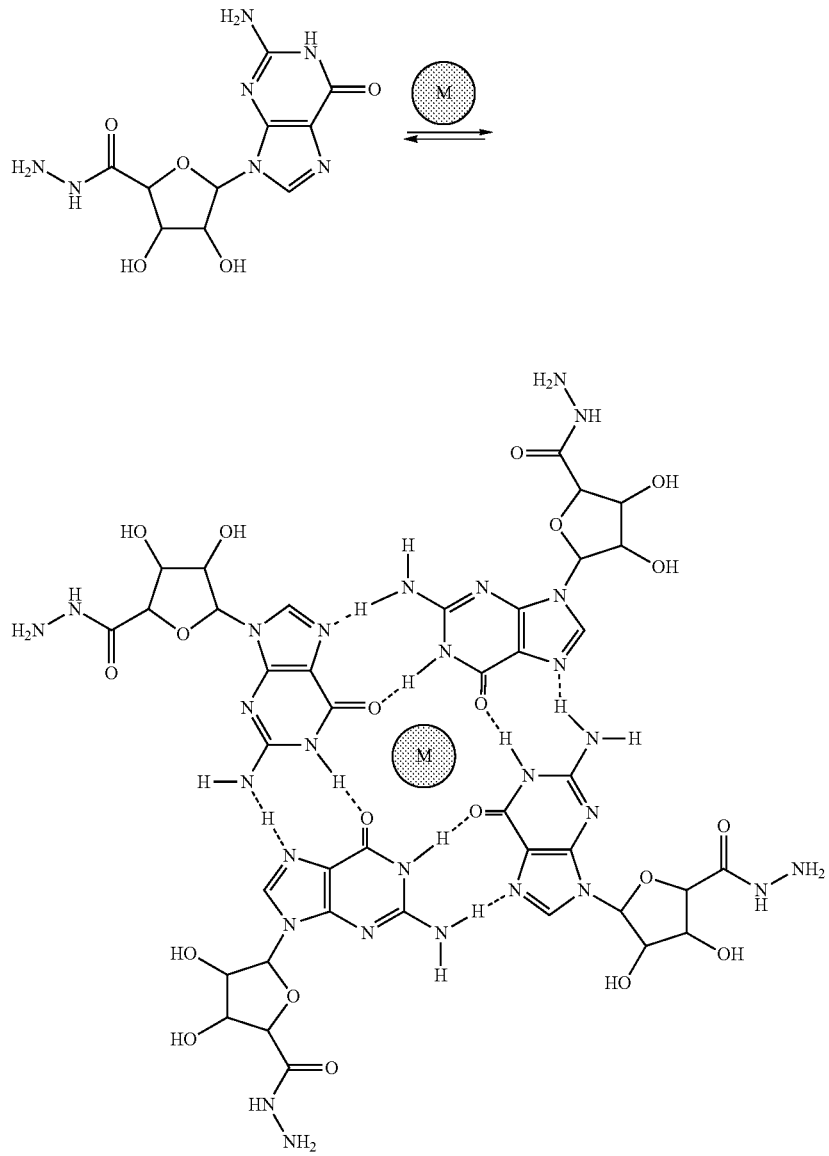

Although the Scheme shows only the syn glycosidic conformation, the guanosine derivatives may adopt both, syn and/or anti glycosidic conformations in the supramolecular structure. The cations can be bound at various stoichiometric ratios depending on the combination of the different possible sites that are occupied. The stereocenters of the compounds are not specified, but can either be in R or S configuration.

The hydrogels according to the present invention were found to be useful as carriers for active substances, which are protected from degradation by the gel matrix and which can be released in a controlled manner to the environment.

Therefore another object of the present invention is an active gel obtainable by admixing together:

at least one active substance, and a gel as above described or its constituents as above described.

As mentioned above, an active substance is an ingredient having, in particular, a perfuming, flavoring, pharmaceutical, insect repellent or attractant, insecticide, antibacterial, agrochemical effect and mixtures thereof.

In a preferred embodiment of the present invention, the active substance is a flavoring ingredient, a perfuming ingredient, a pharmaceutical ingredient, or an agrochemical. A pharmaceutical ingredient may be a drug, such as a medicament for humans or animals or vitamins. An agrochemical may be an herbicide, a pesticide or a fungicide.

As mentioned above, the concentration of the compound of formula (I), as well as that of the salt and the active substance influences the temperature of gelation and a person skilled in the art may want to choose these concentrations in order to obtain a particular gelation temperature suitable for the targeted application.

The active substance can be a neutral compound or an organic salt.

The active substances can be $C_5$-$C_{30}$ aliphatic or aromatic, hydrocarbons, aldehydes, ketones, carboxylic esters, lactones, nitrites, ethers, amines, or alcohols, as well as mixtures thereof. Preferably, the active substance is a $C_5$-$C_{30}$ aldehyde or ketone. In the case of pharmaceuticals or agrochemicals the active substance can comprise up to 70 C-atoms.

The active substances is believed to interact with the gel so that their ability to diffuse with the surroundings is modified. For example, when the active substance is an aldehyde or ketone derivative, the substance can reversibly react with the —$NH_2$ group of the hydrazide function of the gel to form a hydrazone derivative which is believed to be in an equilibrium with the free hydrazide function, as illustrated in Scheme 2.

Scheme 2: Formation of reversible adducts between the G-quartet of the gel and an active aldehyde or ketone.

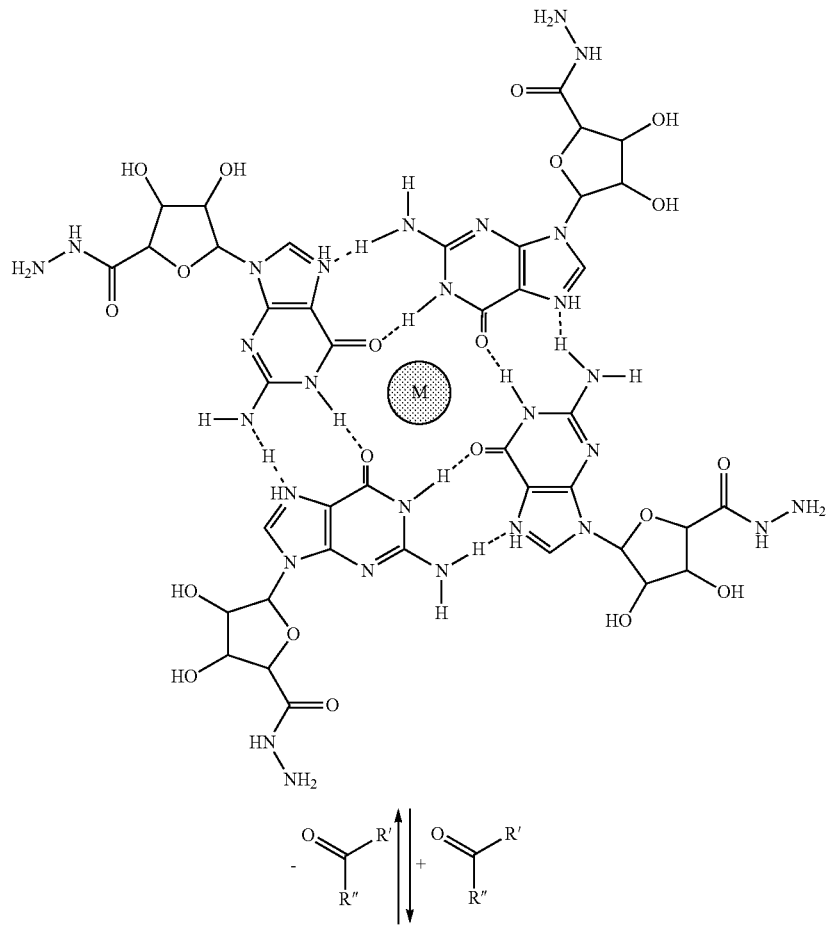

-continued

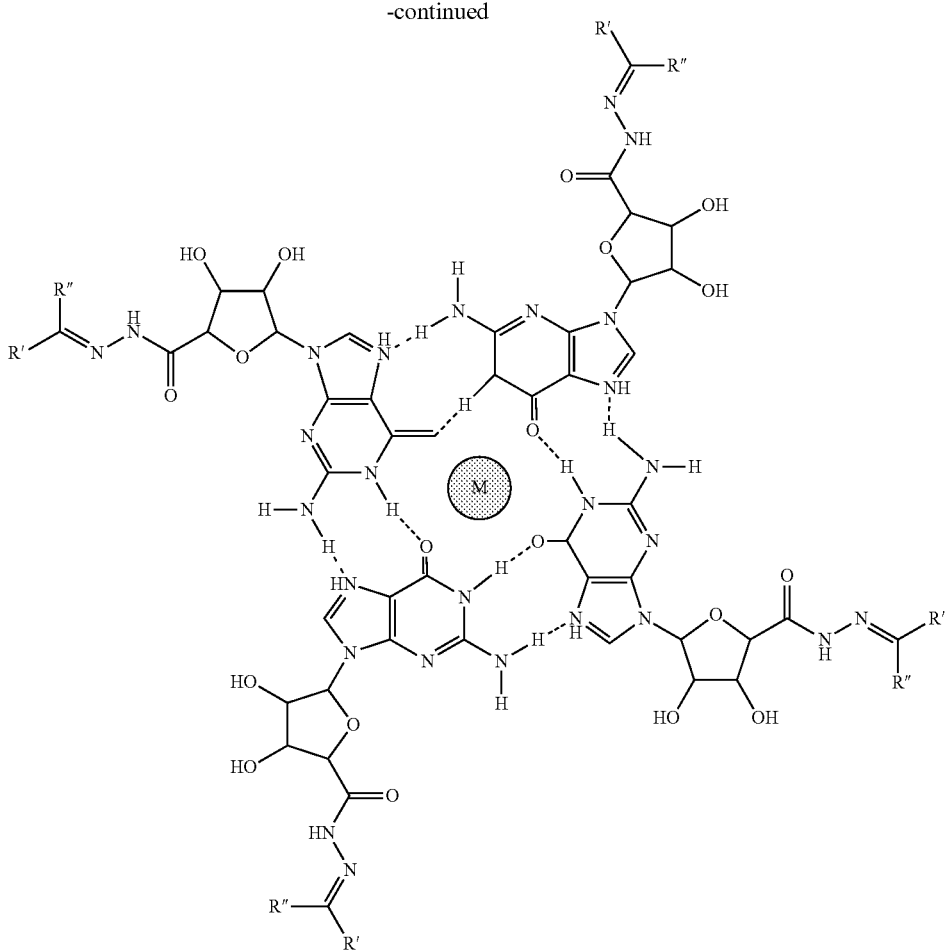

Acylhydrazone derivatives of compounds of formula (I) can alternatively be prepared separately by reaction with active aldehydes or ketones and then be added to the gel either in their pure form or in a mixture with a compound of formula (I) and other active aldehydes and/or ketones. The formation of this equilibrium results in stronger retention of the active compound in the gel. Alternatively the active substance can be included in the gel structure without covalent binding to the compound (I).

The retention allows to protect the active substance from an external aggressive medium and also to deliver the active substance in a controlled manner or rate. Active compounds can thus be covalently or non-covalently included into the supramolecular hydrogel structure.

According to a particular embodiment of the invention, the active substance is a perfuming ingredient. By "perfuming ingredient" it is meant here a compound, which is used in perfuming preparation or composition to impart a hedonic effect. In other words such ingredient, to be considered as being a perfuming one, must be recognized by a person skilled in the art as being able to impart or modify in a positive or pleasant way the odor of a composition, and not just as having an odor. Examples of such ingredients can be found in reference texts such as the book by S. Arctander, Perfume and Flavor Chemicals, 1969, Montclair, N.J., USA, or its more recent versions, or in other works of a similar nature, as well as in the abundant patent literature in the field of perfumery.

Particularly useful perfuming ingredients are the perfuming aldehydes or ketones, in particular $C_5$-$C_{30}$ perfuming aldehydes or ketones. As non-limiting examples of the perfuming aldehydes or ketone one may cite the following:

A) aldehydes of formula R'''—CHO wherein R''' is a linear or α-branched alkyl group of $C_8$ to $C_{12}$, benzaldehyde, 1,3-benzodioxol-5-carboxaldehyde (heliotropine), 3-(1,3-benzodioxol-5-yl)-2-methylpropanal, (E)-4-decenal, 8-decenal, 9-decenal, 3-(6,6-dimethyl-bicyclo[3.1.1]hept-2-en-2-yl)propanal, 2,4-dimethyl-3-cyclohexene-1-carbaldehyde (Triplal®, origin: International Flavors and Fragrances, USA), 3,5-dimethyl-3-cyclohexene-1-carbaldehyde, 1-(3,3-dimethyl-1-cyclohexyl)-1-ethanone, 5,9-dimethyl-4,8-decadienal, 2,6-dimethyl-5-heptenal, 3,7-dimethyl-2,6-octadienal (citral), 3,7-dimethyloctanal, 3,7-dimethyl-6-octenal (citronellal), (3,7-dimethyl-6-octenyl)acetaldehyde, 3-dodecenal, (Z)-4-dodecenal, 3-ethoxy-4-hydroxybenzaldehyde (ethylvanillin), 4-ethyl benzaldehyde, 3-(2 and 4-ethylphenyl) 2,2-dimethylpropanal, 2-furancarbaldehyde (furfural), (E)-2-hexyl-3-phenyl-2-propenal (hexylcinnamaldehyde), 7-hydroxy-3,7-dimethyloctanal (hydroxycitronellal), 4-hydroxy-3-methoxybenzaldehyde (vanillin), 4- and 3-(4-hydroxy-4-methylpentyl) 3-cyclohexene-1-carbaldehyde (Lyral®, origin: International Flavors and Fragrances, USA), 4-isopropylbenzaldehyde (cuminaldehyde), 3-(4-isopropylphenyl)-2-methylpropanal, 2-(4-isopropylphenyl)propanal, (4R)-1-p-menthene-9-carbaldehyde (Liminal®, origin: Firmenich SA, Geneva, Switzerland), 2- and 4-methoxybenzaldehyde (anis aldehyde), 6-methoxy-2,6-dimethylheptanal (methoxymelonal), 8(9)-methoxy-tricyclo[5.2.1.0.(2,6)]decane-3(4)-carbaldehyde (Scentenal®, origin: Firmenich SA, Geneva, Switzerland), 1-methyl-4-(4-methyl-3-pentenyl)-3-cyclohexen-1-carbaldehyde (Precyclemone® B, origin: International Flavors & Fragrances, USA), 4-(4-methyl-3-pentenyl)-3-cyclohexene-1-carbaldehyde (Acropal®, origin: Givaudan-Roure SA., Vernier, Switzerland), (4-methylphenoxy)acetaldehyde, (4-methylphenyl)acetaldehyde, 3-methyl-5-phenylpentanal, 2-(1-methylpropyl)-1-cyclohexanone, 2,6-nonadienal, (Z)-6-nonenal, phenoxyacetaldehyde, phenylacetaldehyde, 3-phenylbutanal (Trifernal®, origin: Firmenich SA, Geneva, Switzerland), 3-phenylpropanal, 2-phenylpropanal (hydratropaldehyde), (E)-3-phenyl-2-propenal (cinnamaldehyde), 3-(4-tert-butylphenyl) 2-methylpropanal (Lilial®, origin: Givaudan-Roure SA, Vernier, Switzerland), 3-(4-tert-butylphenyl)propanal (Bourgeonal®, origin: Quest International, Naarden, Netherlands), tricyclo[5.2.1.0(2,6)]decane-4-carbaldehyde, exo-tricyclo[5.2.1.0(2,6)]decane-8exo-carbaldehyde (Vertral®, origin: Dragoco, Germany), 2,6,6-trimethyl-bicyclo[3.1.1]heptane-3-carbaldehyde (formyl pinane), 2,4,6- and 3,5,6-trimethyl-3-cyclohexene-1-carbaldehyde, 2,2,3-trimethyl-3-cyclopentene-1-acetaldehyde (campholenic aldehyde), 2,6,10-trimethyl-2,6,9,11-dodecatetraenal, (E)-2,5,6-trimethyl-4-heptenal, 3,5,5-trimethylhexanal (Verdinal, origin: Quest International, Naarden, Netherlands), 10-undecenal or 9-undecenal and their mixtures such as Intreleven aldehyde (origin: International Flavors & Fragrances, USA), and B) $C_{8-11}$ ketones of formula R'—(CO)—R" wherein R' and R" are linear alkyl groups, acetophenones, damascenones and damascones, 1-(5,5-dimethyl-1-cyclohexen-1-yl)-4-penten-1-one (Neobutenone®, origin: Firmenich SA, Geneva, Switzerland), 4-(1,1-dimethylpropyl)-1-cyclohexanone (Orivone®, origin: International Flavors & Fragrances, USA), 2,4-di-tert-butyl-1-cyclohexanone, 2-hexyl-1-cyclopentanone, 2-hydroxy-3-methyl-2-cyclopenten-1-one, 4-(4-hydroxy-1-phenyl)-2-butanone (raspberry ketone), ionones and methyl ionones, irones, 4-isopropyl-2-cyclohexen-1-one, macrocyclic ketones such as, for example, cyclopentadecanone (Exaltone®) or 3-methyl-4-cyclopentadecen-1-one and 3-methyl-5-cyclopentadecen-1-one (Delta Muscenone) or 3-methyl-1-cyclopentadecanone (Muscone) all from Firmenich SA, Geneva, Switzerland, 1(6),8-p-menthadien-2-one (carvone), 1-(1-p-menthen-2-yl)-1-propanone, menthone, (1 R,4R)-8-mercapto-3-p-menthanone, 7-methyl-2H,4H-1,5-benzodioxepin-3-one (Calone®, origin: C.A.L. SA, Grasse, France), 5-methyl-3-heptanone, 6-methyl-5-hepten-2-one, methyl 3-oxo-2-pentyl-1-cyclopentaneacetate (Hedione®, origin: Firmenich SA, Geneva, Switzerland), 5-methyl-exo-tricyclo[6.2.1.0(2,7)]undecan-4-one, 2-naphthalenyl-1-ethanone, 1-(octahydro-2,3,8,8-tetrame-2-naphthalenyl)-1-ethanone (isomeric mixture, Iso E Super®, origin: International Flavors & Fragrances, USA), 2-pentyl-1-cyclopentanone (Delphone), 4-phenyl-2-butanone (benzyl acetone), 2-tert-butyl-1-cyclohexanone, 2,4,4,7-tetramethyl-6-octen-3-one, 1,7,7-trimethyl-bicyclo[2.2.1]heptan-2-one (camphor), 4-(2,6,6-trimethyl-2-cyclohexen-1-yl)-2-butanone (dihydroionone), (E)-1-(2,4,4-trimethyl-2-cyclohexen-1-yl)-2-buten-1-one, 1-(3,5,6-trimethyl-3-cyclohexen-1-yl)-1-ethanone, 2,2,5-trimethyl-5-pentyl-1-cyclopentanone.

Furthermore, according to any of the embodiments mentioned above, the perfuming aldehyde or ketone is advantageously characterized by a vapor pressure above 2.0 Pa, as obtained by calculation using the software EPIwin v 3.10 (available at 2000 US Environmental Protection Agency). According to another embodiment the vapor pressure is above 5.0, or even above 7.0 Pa.

By "insect attractant or repellent" it is meant a compound having either a positive or negative effect on insects. Examples of such ingredients can be found in reference texts such or in other works of a similar nature as for example: A. M. El-Sayed, The Pherobase 2005, http://www.pherobase.net.

A person skilled in the art will be perfectly able to choose the ingredients, as well as their concentrations, needed for the manufacture of an active substance imparting the desired benefits and, at the same time, allowing the formation of the invention's gel.

As non-limiting examples of particularly useful pharmaceutical ingredients one may cite the following: antiviral compounds, such as acyclovir its derivates (valacyclovir, ganciclovir or penciclovir etc.), antibiotics (such as vancomycine, penicilline), vitamins (such as vitamin A, B, C etc.), DNA or RNA, $C_5$-$C_{20}$ natural compounds having a therapeutical effect, $C_5$-$C_{20}$ amino acids and peptides, proteins, and $C_6$-$C_{20}$ carbohydrate based drugs.

Although above we made a particular emphasis on biologically active substrate, it is worth to mention that the active substance can be ionophores, thickeners or liquid crystals.

The compositions of the invention may contain the active substance in an amount comprised between 0.5% and 50%, the percentages being relative to the total weight of the composition. In a preferred embodiment of the invention, the active substance is present in an amount comprised between 1% and 25%, and even more preferably in an amount comprised between 1% and 10%.

With respect to the compound of formula (I), the active substance is preferably added in a molar ratio varying between 0.01 and 2 equivalents, or even more preferably in a molar ratio comprised between 0.1 and 1 equivalents.

As anticipated above, the hydrogel composition of the invention is particularly suitable for the manufacture of a consumer article for dispensing a volatile material in the surrounding space. Thus, a consumer article containing, or associated with, a gel composition according to the invention is also an object of the present invention.

Such a consumer article can be, depending on the nature of the volatile liquid component used in the preparation of the gel composition, a perfuming or sanitizing device such as an air freshener, particularly of the solid or gel type, a diaper pail freshener, a car freshener, a closet freshener, a cat litter box freshener, a shoe freshener or a garbage pail freshener, a toothpaste, a cosmetic or pharmaceutical cream, a hair care or body care product, a cleaning product, a surface polishing article, an insecticide or an insect attractant or repellent device.

The consumer article of the invention, to the contrary of those of the prior art previously cited, can simply consist in the invention gel composition, molded in an appropriate shape, i.e. a support of the gel is not required. The gel composition of the invention may have any suitable shape.

It is also understood that the invention's gel may also be associated with a container housing the composition. In such a case, different types of containers can be used. As non limiting examples, one can cite a container made of a material totally impermeable to the vapors of the volatile liquid component and which possesses at least an aperture through which the vapors of the volatile liquid component can be diffused into the air surrounding the consumer article. Alternatively, the container can envelope entirely the gel and at least a portion of the container is made of a material which allows the escape of the vapors of the volatile liquid component into the air surrounding the consumer article.

Whatever or not the consumer article includes a container, in order to prevent diffusion of vapors of the volatile liquid into the surroundings during storage, the consumer article, or the portion of the container which is permeable to the volatile liquid's vapors, can be sealed by any known means, such as a plastic film, which is impermeable to the volatile liquid phase vapors. The consumer will then activate the consumer article simply by removing the sealing, after which the volatile liquid phase will start to diffuse into the surrounding air.

The compound of formula (I) can be synthesized from commercially available starting materials in a reaction sequence as illustrated for the example of guanosine-5'-hydrazide in Scheme 3.

were recorded in DMSO-$d_6$ or $D_2O$ on a Bruker-Biospin spectrometer at 400 MHz for $^1H$ and at 100.6 MHz for $^{13}C$, or on a Bruker AV 500 spectrometer at 500 MHz for $^1H$ and at 125.8 MHz for $^{13}C$, the chemical displacements δ are indicated in ppm with respect to TMS as the standard if not mentioned otherwise, the coupling constants J are expressed in Hz. Electrospray ionisation mass spectrometry (ESI-MS) was carried out on a Bruker Micro-TOF mass spectrometer coupled with liquid chromatography. Samples were prepared at a concentration of 200 µM in Milli-Q water or in 0.5 M ammonium acetate buffer. Prior to injection, a small aliquot of the sample was diluted 20-fold and used for ESI-MS. The following mild conditions were used to detect the supramolecular assembly of G-quartets: dry heater temperature set at 120° C., ion polarity positive, nebulizer pressure 0.4 bar, capillary voltage 4000 V, end plate offset voltage −400V, and Scheme 3: Example for the preparation of a hydrogelator according to the invention

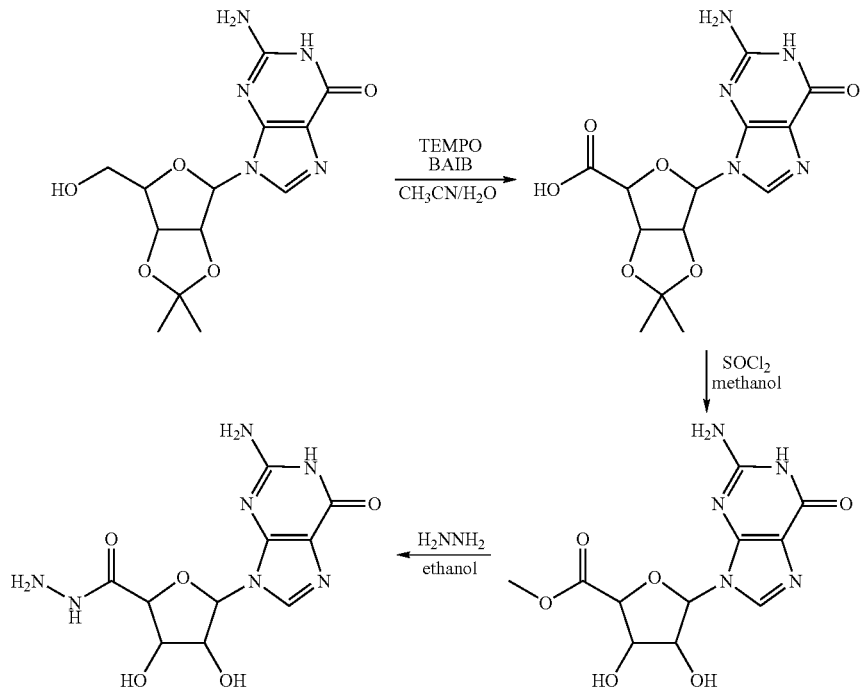

After suitable protection of the free hydroxyl groups in the 3 and 4 positions, as for example in the form of a ketal, the free hydroxymethyl group is oxidized to the corresponding carboxylic acid. Suitable oxidation conditions are for example those described by Epp and Widlanski (J. Org. Chem., 1999, 64, 293-295) using the 2,2,6,6-tetramethyl-1-piperidinyloxyl (TEMPO) radical and [bis(acetoxy)iodo]benzene (BAIB) in aqueous acetonitrile. The carboxylic acid can then be transformed to the corresponding methyl ester with $SOCl_2$ in methanol (see for example: Norris et al., Nucl. Acid. Res., 1975, 2, 1093-1100), followed by treatment with hydrazine hydrate in ethanol or methanol (see for example: Vercruysse et al., Bioconjugate Chem., 1997, 8, 686-694).

EXAMPLES

The following examples are further illustrative of the present invention embodiments, and further demonstrate the advantages of the invention relative to prior art teachings.

In these examples, the abbreviations have the usual meaning in the art. If not stated otherwise, the NMR spectral data dry gas flow 3.0 L/min. Viscosity measurements were performed on Brookfield Digital-Rheometer, Model DV-III fitted with a spindle model CPE 40 of 4 cm diameter and 1° angle.

Example 1

Preparation of Guanosine-5'-Hydrazide

To a suspension of guanosine-5'-methyl ester (methyl (2S, 3S,4R,5R)-5-(2-amino-6-oxo-1,6-dihydro-9H-purin-9-yl)-3,4-dihydroxytetrahydro-2-furancarboxylate, 100 mg, 0.32 mmol) in methanol (150 ml) was added hydrazine hydrate (80 mg, 1.6 mmol) and the mixture was refluxed for 12 h. The reaction mixture was concentrated to ⅓ of its volume, filtered and dried under vacuum to give 76 mg of guanosine-5'-hydrazide ((2S,3S,4R,5R)-5-(2-amino-6-oxo-1,6-dihydro-9H-purin-9-yl)-3,4-dihydroxytetrahydro-2-furancarbohydrazide, yield 76%).

White solid. M.p.: 241-243° C.

$^1$H NMR: (400 MHz, DMSO-$d_6$) 10.8 (br. s, 1 H); 10.6 (br. s, 1 H); 7.94 (s, 1 H); 6.59 (br. s, 2 H); 5.77 (d, J=7.6, 1 H); 5.73 (m, 1 H); 5.54 (m, 1 H); 4.50 (m, 1 H); 4.45 (m, 1 H); 4.33 (d, J=1.2, 1 H); 4.0 (s, 1 H).

$^{13}$C NMR: (100.6 MHz, DMSO-$d_6$) 169.2 (s); 157.1 (s); 153.9 (s); 150.3 (s); 137.7 (d); 117.8 (s); 88.0 (d); 84.6 (d); 73.5 (d); 72.6 (d).

ESI-MS: 312.1 [M+H]$^+$.

Preparation of the Benzaldehyde Derivative of Guanosine-5'-Hydrazide

A suspension of guanosine-5'-hydrazide (300 mg, 0.96 mmol) and benzaldehyde (153 mg, 1.45 mmol) in ethanol (10 ml) was refluxed for 6 h. After cooling to room temperature the mixture was filtered to give 250 mg of the corresponding hydrazone ((2S,3S,4R,5R)-5-(2-amino-6-oxo-1,6-dihydro-9H-purin-9-yl)-3,4-dihydroxytetrahydro-2-furancarboxylic acid benzylidene hydrazide, yield 74%) as a mixture of two isomers with respect to the amide bond conformation (syn/anti ca. 64:36). Gray solid.

$^1$H NMR: (400 MHz, DMSO-$d_6$, major isomer): 11.69 (s, 1 H); 10.88 (s, 1 H); 8.35 (s, 1 H); 8.28 (s, 1 H); 7.77-7.66 (m, 2 H); 7.54-7.39 (m, 3 H); 6.65 (br. s, 2 H); 5.88 (d, J=6.1, 1 H); 5.67 (br. s, 2 H); 4.61 (dd, J=6.1, 1.0, 1 H); 4.47 (d, J=3.1, 1 H); 4.31 (dd, J=3.1, 1.0, 1 H); (minor isomer): 11.72 (s, 1 H); 10.81 (s, 1 H); 8.39 (s, 1 H); 8.05 (s, 1 H); 7.77-7.66 (m, 2 H); 7.54-7.39 (m, 3 H); 6.65 (br. s, 2 H); 5.96 (d, J=7.2, 1 H); 5.67 (br. s, 2 H); 5.34 (m, 1 H); 4.43 (dd, J=4.1, 3.1, 1 H); 4.26 (m, 1 H).

$^{13}$C NMR: (100.6 MHz, DMSO-$d_6$, major isomer) 166.5 (s); 156.7 (s); 154.4 (s); 151.5 (s); 149.5 (d); 136.2 (d); 134.4 (s); 130.7 (d); 129.2 (d); 127.6 (d); 116.2 (s); 87.3 (d); 83.2 (d); 73.7 (d); 73.4 (d); (minor isomer) 171.5 (s); 156.7 (s); 154.4 (s); 152.0 (s); 144.8 (d); 135.7 (d); 134.3 (s); 130.5 (d); 129.2 (d); 127.4 (d); 115.6 (s); 86.2 (d); 81.4 (d); 75.2 (d); 73.7 (d).

ESI-MS: 401 [M+2]$^+$, 400 [M+H]$^+$.

Example 2

Preparation of Gels and Measurement of Gel Melting Temperatures

Guanosine-5'-hydrazide was dissolved in a 0.5 M acetate buffer pH 6 (500 µL) to make up 15 mM concentration. The container was heated until guanosine-5'-hydrazide completely dissolved, and was then cooled to room temperature. Gelation was observed and the gel melting temperature ($T_{gel}$) was determined visually by the vial inversion method. The sample vials were immersed in an inverted position in an oil bath and the temperature was increased slowly. $T_{gel}$ was taken as the point where the gel started to flow.

Guanosine-5'-hydrazide, was found to form stable free standing gels at 15 mM in the presence of Na$^+$, K$^+$ NH$_4^+$ as well as of the much larger (CH$_3$)$_4$N +cation at neutral pH (phosphate buffer). The hydrogels were strong enough not to flow on inversion of the container and were found to be stable at room temperature for several days. ESI-MS showed a peak for (G$_4$+Na) at m/z 1267.4, confirming the identity of the G-quartet. The transmission electron microscopy observation of the gel prepared from revealed fibers of several micrometers in length. The temperatures of gelation $T_{gel}$ were measured at pH 6 in sodium acetate buffer (0.5 M) as a function of gelator concentration. The results indicated that guanosine-5'-hydrazide was able to gelate the buffer solution even at a concentration as low as 10 mM, i.e. about 0.3 wt %, giving $T_{gel}$ of 33° C. At 50 mM, $T_{gel}$ was 65° C., and increasing the concentration up to 100 mM gave product precipitation. The hydrogel formed was thermally reversible but unstable to shear. Determination of $T_{gel}$ as a function of the concentration of guanosine-5'-hydrazide for different cations, showed that K$^+$ was the most efficient gelator/G$_4$ assembler. The other cations showed the sequence of gelation efficiency (CH$_3$)$_4$N$^+$>NH$_4^+$>Na$^+$. The gelation temperature $T_{gel}$ of guanosine-5'-hydrazide, determined visually by container inversion, as a function of K$^+$ concentration, remained unchanged at 61° C. above 45 mM and up to 90 mM salt, indicating that it was independent of ion concentration once gelation was complete.

Example 3

Determination of Guanosine-5'-Gydrazide Gelation by Proton NMR Spectroscopy

To a NMR tube was added guanosine-5'-hydrazide (2.3 mg), D$_2$O (450 µL), 45 µL of KCl stock solution (1 M), 5 µL of dioxane stock solution (300 mM), yielding a 15 mM guanosine-5'-hydrazide, 90 mM KCl and 3 mM dioxane solution. The NMR tube was gently heated until guanosine-5'-hydrazide dissolved and was then cooled to room temperature. The $^1$H NMR spectra (400 MHz) were recorded once the sample was fully gelated. The percentage of free hydrogelator was determined by integrating the proton signal of H-8 on the guanine group with respect to the internal dioxane reference. The proton signal of H-8 is sharp for free guanosine-5'-hydrazide in solution, whereas that for guanosine-5'-hydrazide engaged in the gel it is broadened beyond detection. Integration of the observable H-8 signal with respect to the internal reference (3 mM dioxane) gave the fraction of guanosine-5'-hydrazide still free and in the gel (by difference). The gel was destroyed by addition of a drop of concentrated DCl giving a clear solution, and then the proton NMR spectrum was recorded; the integration of H-8 of guanosine-5'-hydrazide (100% free in the solution) with respect to the internal dioxane reference gave the amount of guanosine-5'-hydrazide. The difference between the integral of total free guanosine-5'-hydrazide (100% in solution) and the integral of free guanosine-5'-hydrazide in the gelated solution yielded the percentage of gelation.

It was found that practically total gelation (>98%) occurred above about 45 mM KCl. Similarly, the variation of the fraction of free guanosine-5'-hydrazide as a function of temperature was followed by integration of the H-8 proton signal. It displays a sigmoidal shape similar to the melting curve of double stranded DNA, yielding a transition temperature $T_t$ of 43° C.

The difference between the visually determined $T_{gel}$ (61° C.) and $T_t$ (43° C.) may be ascribed to the fact that they concern two different events. Different physical methods refer to different microscopic processes (Terech et al., J. Colloid Interface Sci., 2000, 227, 363-370). $T_t$ refers to the variation at the molecular level of the amounts of free and bound (in the gel) states of 1, possibly involving motions within fibrils without depolymerization. $T_{gel}$ describes the gel-to-sol transition at the macroscopic level, when the material flows under gravity shear due to loss of cohesion of the assembly. In line, the NMR data indicate full melting of the gel at about 55-60° C. Such data may be of much interest for the understanding of the relationship between microscopic and macroscopic collective events in gels and organized phases in general. They also point to the fact that motion within or exchange in and out of an organized phase may occur before phase transition, a feature of significance for delivery processes.

Example 4

Interaction between Active Aldehydes or Ketones and a Guanosine-5'-Hydrazide Based Gel and Formation of the Most Stable Hydrogels To investigate the evolution of the system toward the "best fit" dynamic hydrogel, the hydrazides guanosine-5'-hydrazide (1) and N-(1-hydrazinocarbonyl-2-hydroxy-ethyl)-acetamide (serine hydrazide) (2) and the aldehydes 2-formyl-benzenesulfonic acid sodium salt (3) and phosphoric acid mono-(4-formyl-5-hydroxy-6-methyl-pyridin-3-ylmethyl) ester (pyridoxal monophosphate) (4) were selected. The dynamic library was generated at 15 mM concentration for each compound, at pD 6 in sodium acetate buffer, consists of four possible acylhydrazones A-D (A: 1+3, B: 1+4, C: 2+3, D: 2+4), each presenting two configurational isomers, undergoing continuously interchange by acylhydrazone bond formation and cleavage in aqueous medium. Stock solutions (150 mM) of hydrazide 2 and aldehydes 3 and 4 were prepared by dissolving a given compound in $D_2O$ or deuterated buffer solution. (0.5 M sodium acetate or potassium acetate, pD 6.0). Guanosine-5'-hydrazide (1, 2.3 mg) was dissolved in 500 μL buffer in a NMR tube to make up a 15 mM solution. Then, were added 50 μL of hydrazide 2 solutions, and 50 μL of aldehyde (3, 4) solutions from the stock solutions. The NMR tube was gently heated to 50-60° C. for 5-6 h to reach equilibrium. Then, it was cooled to room temperature and the $^1$H-NMR spectrum (400 MHz) was recorded once the solution was fully gelated. The CH=N imine proton signals of free (non gelated) acylhydrozones, which although broadened, could be clearly identified for each constituent of the mixture. The anti and syn isomers of each acylhydrazone (with respect to the amide bond conformation, about 75% anti and 25% syn ±10% depending on the compound) were integrated, giving the fraction of the library constituents present free in solution. The fraction of guanosine-5'-acylhydrazone in the gel was obtained by difference. Although the acylhydrazone A (1+3) does not give a gel when taken alone, a small amount (≦3%) of it could be trapped in the gel formed by the acylhydrazone B (1+4) in the mixtures of (1+2) with (3+4). The spectra of the individual acylhydrazones (15 mM) showed a weak signal (≦5%) of unreacted aldehyde proton. On heating, the CH=N signals broadened both for the individual compounds and for the mixtures.

A markedly uneven distribution was obtained as shown in FIG. 1. The guanosine-5'-hydrazide 1 gave 8% and 39% of the acylhydrazones A and B, resulting from its reaction with aldehyde 3 and 4, respectively. Similarly, the serine hydrazide 2 reacted with aldehydes 3 and 4 to give about 42% of C as well as 11% of D. When the $^1$H NMR spectra were measured at 55° C., the distribution of acylhydrazones was found be become less uneven. On further temperature increase up to 80° C., the gel was completely melted and the distribution of acylhydrazones was close to equal (FIG. 1). Cooling the reaction mixture slowly over a period of 60 min back to 25° C. restored the initial distribution, indicating that a selection process occurred, by which the mixture evolved to favor the constituent B forming a thermodynamically stable dynamic hydrogel, over constituents A, C and D that do not give such an organized phase. As indicated by the $^1$H-NMR data, two hydrazones B (in the gel) and C (free in solution) clearly dominate in the constitutional dynamic library at equilibrium. The latter is expressed as "image" of B, as a consequence of D being depressed by the trapping of pyridoxal monophosphate 4 in B in the gel. The dynamic selection is reversible and depends on the temperature: at high temperature when the gel has melted the selection disappears, while it operates at 25° C. where the medium is gelated. Thus, there is strong selection when the gel is formed, wherein the guanosine derivative interacts, or reacts with the aldehyde which allow the formation of the most stable product. This principle is confirmed by the replacement of serine hydrazide 2 by the corresponding alanine hydrazide, which results in almost the same distribution of acylhydrazones.

Several control experiments were performed. Equimolar amounts of hydrazide 2 and aldehydes 3 and 4 (1:1:1) gave 15% of acylhydrazone C and 85% of hydrazone D, indicating that hydrazide 2 forms preferentially acylhydrazone D with aldehyde 4. As expected, hydrazide 2 and aldehydes 3 and 4 in a 2:1:1 ratio generate equal amounts of acylhydrazones C and D at equilibrium. Aldehyde 4 and hydrazides 1 and 2 in 1:1:1 molar ratio resulted in gel formation giving 87% acylhydrazone B and 13% of D at equilibrium. Taken together these results stress the ability of gelation to redirect the acylhydrazone distribution, as hydrazide 1 is able to scavenge 4 from 2 in D despite the strong preference of 2 for 4. Reacting 1, 2 with 3 (1:1:1) gave almost equal distribution of imines, as no gelation occurs to drive a selection. These experiments highlight that the guanosine-5'-hydrazide (1) cation-templated self-assembly drives component selection enforced by the ability of the supramolecular assembly B to form a stable hydrogel.

Rheological measurements on the gels formed by the acylhydrazone derivatives of guanosine-5'-hydrazide obtained from pyridoxal monophosphate (4) and 1-formyl furan-3-sulfonic acid indicated that they had a much higher viscosity (2400 mPas and 1900 mPas respectively at 0.38 turn $s^{-1}$ shear rate) than the gel formed by the guanosine-5'-hydrazide itself and that they presented both thermal and shear stress reversibility.

Example 5

Formation of Hydrogels Containing Active Aldehydes or Ketones

The active aldehydes or ketones used in this example are known as perfuming or flavoring ingredients. However, they are also representative as insect repellants or attractants, or as bactericides or fungicides. Some of the compounds such as benzaldehyde, 2,4-dimethyl-3-cyclohexene-1-carbaldehyde (Triplal®), 3,7-dimethyl-6-octenal (citronellal), 2-furancarbaldehyde (furfural), 4-hydroxy-3-methoxybenzaldehyde (vanillin), menthone, 1-(4-methylphenyl)-1-ethanone (4-methylacetophenone), 2-pentyl-1-cyclopentanone (Delphone), 3-phenyl-2-propenal (cinnamaldehyde), or 10-undecenal, have insect attractant or repellent properties (see for example: A. M. El-Sayed, The Pherobase 2005, http://www.pherobase.net) and/or are known to be active against bacteria (see for example: WO 01/24769 or EP 1 043 968).

A 0.5 M potassium acetate buffer (pH 6) was prepared from potassium acetate (4.61 g), glacial acetic acid (0.16 g) and demineralized water (97.11 g, filled up to 100 ml). A pH value of 5.95 (±0.045) was measured at 25° C.

In a small glass container, guanosine-5'-hydrazide (37.3 mg, 0.12 mmol) was dissolved upon sonication in 7 mL of the above described 0.5 M potassium acetate buffer solution. The container was heated on a water bath (at ca. 70° C.) until the hydrazide completely dissolved, then 1 mL of the active aldehyde or ketone (0.06 M) dissolved in the potassium acetate buffer was added, yielding a 15 mM guanosine-5'-hydrazide and a 7.5 mM aldehyde or ketone solution. The sample was left cooling to room temperature. In a comparison experiment non-functionalized guanosine (33.8 mg, 0.12 mmol) was used instead of guanosine-5'-hydrazide. To see whether a gel was obtained or whether the compound precipitated, the samples were inverted and/or analyzed visually after cooling to room temperature and after being standing at room temperature for 5 days.

The following results were obtained:

| Aldehyde or ketone | guanosine-5'-hydrazide | | guanosine | |
|---|---|---|---|---|
| | after cooling | after 5 d | after cooling | after 5 d |
| Vanillin | gel | gel | unstable gel | precipitate |
| Delphone | gel | gel | precipitate | precipitate |
| α-Damascone | gel | gel | precipitate | precipitate |
| Hedione ® | gel | gel | precipitate | precipitate |
| Lilial ® | gel | unstable gel[1)] | unstable gel | precipitate |
| Trifernal ® | gel | unstable gel | unstable gel | precipitate |
| 3,5,5-Trimethylhexanal | unstable gel | unstable gel | precipitate | precipitate |
| (−)-Menthone | gel | gel | precipitate | precipitate |
| Benzaldehyde | gel | gel | precipitate | precipitate |
| Furfural | gel | gel | unstable gel | precipitate |
| 4-Methylacetophenone | gel | gel | unstable gel | precipitate |
| 10-Undecanal | gel | gel | unstable gel | precipitate |
| Citronellal | gel | gel | unstable gel | precipitate |
| Triplal ® | unstable gel | unstable gel | unstable gel | precipitate |
| Cinnamaldehyde | gel | gel | unstable gel | precipitate |
| Benzyl acetone | unstable gel | gel | precipitate | precipitate |

[1)]low viscosity gel

To investigate the formation of gels with mixtures of active aldehydes and/or ketones 0.075 mol of three different aldehydes or ketones, respectively, were dissolved in 20 mL of the above described 0.5 M potassium acetate buffer. In a small glass container, guanosine-5'-hydrazide (37.1 mg, 0.12 mmol) was dissolved upon sonication in 8 mL of the 0.5 M potassium acetate buffer solution containing the aldehydes, yielding a 15 mM guanosine-5'-hydrazide and a 3.75 mM solution for each aldehyde or ketone. The container was heated on a water bath (at ca. 70° C.) and then left cooling to room temperature. In a comparison experiment non-functionalized guanosine (33.8 mg, 0.12 mmol) was used instead of guanosine-5'-hydrazide. To see whether a gel was obtained or whether the compound precipitated, the samples were inverted and/or analyzed visually after 1 day and after being standing at room temperature for 5 days.

The following results were obtained:

| Aldehydes or ketones | guanosine-5'-hydrazide | | guanosine | |
|---|---|---|---|---|
| | after 1 d | after 5 d | after 1 d | after 5 d |
| Benzaldehyde Furfural 4-Methylacetophenone | unstable gel | gel | unstable gel | precipitate |
| Benzaldehyde Citronellal 4-Methylacetophenone | gel | gel | precipitate | precipitate |
| Benzaldehyde Citronellal Triplal ® | gel | gel | unstable gel | precipitate |
| 4-Methylacetophenone Citronellal Triplal ® | gel | gel | unstable gel | precipitate |

The data show that in the presence of active aldehydes and ketones gels were obtained when guanosine-5'-hydrazide served as the hydrogelator, whereas the samples using non-functionalized guanosine as the hydrogelator were found to unstable and to precipitate after standing for 5 days.

Example 6

Quantification of the Amount of Active Aldehydes or Ketones Incorporated into the Supramolecular Hydrogel Structure by Proton NMR Spectroscopy Guanosine-5'-hydrazide (37.1 mg, 0.12 mmol) was dissolved in 7 mL of a 0.5 M potassium acetate buffer in $D_2O$ (pD 6). Then different amounts of benzaldehyde (31.6 mg, 0.30 mmol; 62.9 mg, 0.59 mmol or 94.7 mg, 0.89 mmol) were dissolved in 5 mL of a 0.5 M potassium acetate buffer in $D_2O$ containing dioxane (60.4 mM) as internal standard. For the measurement 700 μL of the buffer containing guanosine-5'-hydrazide and 100 μL of either one of the benzaldehyde buffer solutions, respectively, were added to a NMR tube together with some sodium 3-trimethylsilyl-tetradeuteriopropionate (as internal lock), yielding a 15 mM guanosine-5'-hydrazide solution with 0.5, 1.0 or 1.5 molar equivalents of benzaldehyde, and 0.5 molar equivalents of dioxane. The tubes were heated on a water bath (ca. 70° C.) until a clear solution was obtained and then left cooling to room temperature overnight.

The resulting product was a fully solidified sample. As shown by the results hereinbelow, it is supposed that the sample was composed essentially of a gellified phase (comprising the non-free components) and a dispersion a liquid phase trapped inside the gel structure (comprising the free components).

The $^1H$ NMR spectra (500 MHz) were recorded on the fully solidified samples. The percentage of free hydrogelator (in mol-%) was determined by integrating the proton signal of H-8 on the guanine group with respect to the internal dioxane reference, that of free benzaldehyde by integrating the H-3 proton signals of the aromatic ring.

In the samples containing 0.5, 1.0 or 1.5 equivalents of benzaldehyde with respect to the amount of guanosine-5'-hydrazide 13.7%, 8.9% and 5.6% of free benzaldehyde and 4.7%, 4.9% and 4.3% of free guanosine-5'-hydrazide were determined in the trapped liquid phase, respectively. After standing at room temperature for 5 d, the NMR samples were re-heated until the gel dissolved and then cooled again to room temperature. Re-measuring the $^1H$ NMR spectra indicated 13.9%, 8.3% and 5.6% of free benzaldehyde and 4.2%, 3.2% and 3.2% of free guanosine-5'-hydrazide, respectively, thus showing good a reproducibility of the gel formation.

The fact that only 5-14% of free benzaldehyde remained in the trapped liquid phase, although it was used in excess with respect to the guanosine-5'-hydrazide in one case, indicates that the active aldehyde or ketone can covalently and/or non-covalently be incorporated into the supramolecular hydrogel structure.

Example 7

Quantification of the Evaporation of Active Aldehydes or Ketones from the Supramolecular Hydrogel Structure by Headspace Analysis In a small glass container, guanosine-5'-hydrazide (42.0 mg, 0.14 mmol) was dissolved upon sonication in 7 mL of a 0.5 M potassium acetate buffer (pH 6). After addition of 1 mL of a solution of non-volatile 2-formylbenzenesulfonic acid sodium salt (200.5 mg, 1.0 mmol) in 10 mL of the buffer solution, the sample was heated on a water bath to ca. 70° C. After complete dissolution, 1 mL of a solution containing equimolar amounts (0.30 mmol) of volatile furfural (29.2 mg), benzaldehyde (31.5 mg), acetophenone (35.7 mg) and 2,4,6-trimethyl-3-cyclohexene-1-carbaldehyde (45.6 mg) in 10 mL of buffer was added to yield a 15 mM guanosine-5'-hydrazide and a 3.3 mM aldehyde or ketone solution. The sample was left cooling to room temperature to form a hydrogel.

In a comparison experiment guanosine (38.1 mg, 0.14 mmol) was used instead of guanosine-5'-hydrazide. The open containers were left standing at room temperature for 17 days. The amount of volatile aldehydes or ketones in the headspace was determined by dynamic headspace analysis after 1, 6 and 17 days, respectively.

For the analysis, the glass containers were put into an headspace sampling cell (ca. 650 mL) and exposed to a constant air flow of about 200 mL/min, respectively. The air was filtered through active charcoal and aspirated through a saturated solution of NaCl. During 15 min the headspace system was left equilibrating, then the volatiles were adsorbed during 20 min (after 1 and 6 days) or 30 min (after 17 days) on a clean Tenax® cartridge, respectively. The sampling was repeated 8 times every 30 min. The cartridges were desorbed on a Perkin Elmer TurboMatrix ATD desorber coupled to a Carlo Erba MFC 500 gas chromatograph equipped with a J&W Scientific DB1 capillary column (30 m, i.d. 0.45 mm, film 0.42 μm) and a FID detector. The volatiles were analyzed using a two step temperature gradient starting from 70° C. to 130° C. at 3° C./min and then going to 260° C. at 25° C./min. The injection temperature was at 240° C., the detector temperature at 260° C. Headspace concentrations (in ng/L) were obtained by external standard calibrations of the corresponding fragrance aldehydes and ketones using ethanol solutions of five different concentrations. 0.2 μl of each calibration solution was injected onto Tenax® cartridges, which were immediately desorbed under the same conditions as those resulting from the headspace sampling. Whereas in the case of guanosine-5'-hydrazide the gel remained stable during the entire experiment, the gel with the guanosine was found to precipitate after a couple of days.

The following average headspace concentrations in ng/L were obtained:

| Aldehyde or ketone | guanosine-5'-hydrazide | | | guanosine | | |
|---|---|---|---|---|---|---|
| | 1 d | 6 d | 17 d | 1 d | 6 d | 17 d |
| Furfural | 341 | 156 | 44 | 662 | 358 | 52 |
| Benzaldehyde | 516 | 83 | 29 | 1968 | 361 | 1 |
| Acetophenone | 948 | 424 | 31 | 1297 | 483 | 13 |
| 2,4,6-Trimethyl-3-cyclohexene-1-carbaldehyde | 99 | 35 | 19 | 1231 | 83 | 0 |

The data show that the incorporation of the active aldehydes and ketones into the hydrogel structure formed with guanosine-5'-hydrazide results in a less pronounced decrease for the concentrations of active aldehydes and ketones in the headspace than this is the case for the gel formed with guanosine. This results in a more constant release of the active substance over time. Furthermore, the higher headspace concentrations (for benzaldehyde, acetophenone and 2,4,6-trimethyl-3-cyclohexene-1-carbaldehyde and about comparable concentrations for furfural) measured at the end of the experiment in the presence of guanosine-5'-hydrazide as compared to the sample with guanosine result in an increased long-lastingness for the release of the active substances.

Example 8

Figure 2:
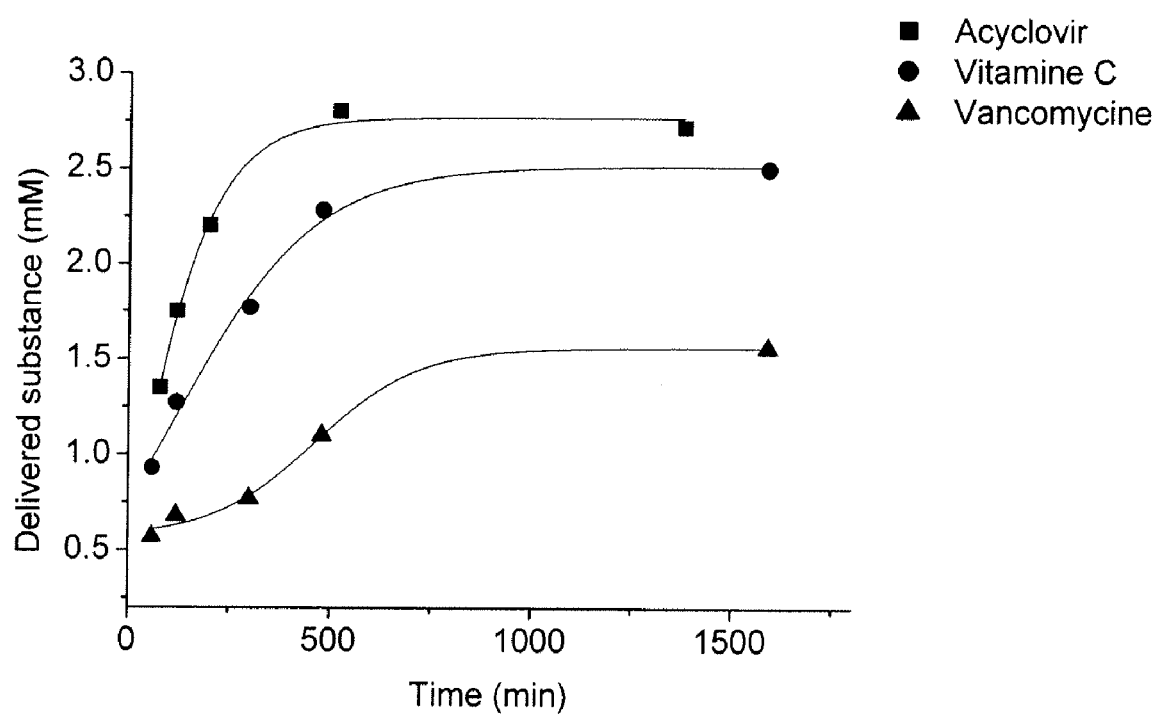
FIG. 2 summarizes the results of example 8 and represents the profile for the release of acyclovir, vitamin C and vancomycine from the hydrogel into the supernatant buffer at different time intervals as determined by $^1$H NMR spectroscopy.

Quantification of the Release of Active Substances from the Supramolecular Hydrogel Structure by Proton NMR Spectroscopy Guanosine-5'-hydrazide and acyclovir were dissolved in a 0.5 M deuterated sodium acetate buffer pD 6 (500 μL) to make up a concentration of 15 mM, and 5 mM respectively. The container was heated until guanosine-5'-hydrazide dissolved completely, and was then cooled to room temperature. After gelation, sodium acetate buffer (500 μL) was added very carefully on the top of the hydrogel. At different time intervals, the supernatant was taken out carefully to an NMR tube. The $^1$H NMR spectra were recorded using tert-butanol (3 mM) as an internal reference. The percentage of acyclovir released from the hydrogel was determined by integrating the H-8 proton signal of the guanine moiety of acyclovir with respect to the tert-butanol signal. In a separate NMR tube, acyclovir and tert-butanol were dissolved in $D_2O$ (500 μL) to make up 5 mM and 3 mM solutions, respectively, and a proton NMR spectrum was recorded. The integration of the H-8 proton signal of the guanine moiety of acyclovir with respect to internal tert-butanol (3 mM) gave the total amount of acyclovir (corresponding to 100%). The difference between the integral of total amount of acyclovir and the integral of acyclovir released from the hydrogel into the supernatant buffers at various time intervals gave the percentage of the released active substance. Similar experiments using vancomycine or Vitamin C as the active substance have been carried out. The amounts of the respective active substances released into the supernatant buffer at different times are shown in FIG. 2.

Example 9

Formation of a Hydrogel Containing the Benzaldehyde Derivative of Guanosine-5'-Hydrazide In a small glass container, guanosine-5'-hydrazide (46.9 mg, 0.15 mmol) was dissolved upon sonication in 10 mL of the above described 0.5 M potassium acetate buffer solution. The container was heated on a water bath (at ca. 70° C.) until the hydrazide completely dissolved. 6 mL of this solution were then added to 2 mL of 5-(2-amino-6-oxo-1,6-dihydro-9H-purin-9-yl)-3,4-dihydroxytetrahydro-2-furancarboxylic acid benzylidene hydrazide (11.8 mg, 0.03 mmol) dissolved in the potassium acetate buffer at ca. 70° C., yielding a sample being 11.3 mM in guanosine-5'-hydrazide and 3.7 mM in the benzylidene hydrazide derivative. The sample was left cooling to room temperature. The sample was inverted and/or analyzed visually after being standing at room temperature for 1 and for 5 days. A gel was obtained.

What is claimed is:
1. A gel comprising:
1) at least one compound of formula

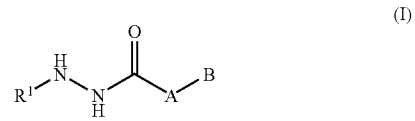

(I)

wherein $R^1$ represents a hydrogen atom, a $C_1$-$C_{10}$ linear or branched alkyl group or a phenyl group;
A is selected from the group consisting of formulae i) to vi), i)

ii)

iii)

iv)

v)

vi)

in which formulae the dotted and the bold lines indicate the connection to the —CONHNHR¹ and B moieties, respectively, and R², R³ or R⁴ are, independently from each others, selected from the group consisting of —H, —OH, —OCOCH₃, —OCH₂Ph, —OPO₃NaH, and —OPO₃H₂, or, taken two of them together, of —OP(OH)OO—, —OP(ONa)OO—, and —OC(CH₃)₂O—; and Y and X are a NH group or oxygen atom or a CH₂ or CHOH group; and n is an integer varying from 1 to 50; and B is a moiety of formulae vii) to x)

vii)

viii)

ix)

x)

in which formulae the bold line indicates the connection to the A moiety, and R⁵ is selected from the group consisting of —H, —OH, —OCH₃, —SH, —SCH₃, —NH₂, —NHCH₃, —OCOCH₃, —OCH₂Ph, —OCH₂CH=CH₂, and —Br;

2) a salt comprising at least one cation selected from the group consisting of K⁺, Na⁺, Li⁺, Rb⁺, Cs⁺, Sr²⁺, Ba²⁺, NH₄⁺ or (CH₃)₄N⁺, and at least one anion selected from the group consisting of Cl⁻, Br⁻, I⁻, NO₃⁻, HCOO⁻, CH₃COO⁻, H₂PO₃⁻, HPO₃²⁻, PO₃³⁻, SO₄²⁻, CO₃²⁻, HCO₃⁻, BO₂⁻, PF₆⁻, picrate⁻ and citrate³⁻; and 3) a water-based liquid.

2. The gel according to claim 1, wherein, in the compound of formula (I), A is selected from formulae i) or ii), with R² and R³ being independently of each others —H or —OH, B is a moiety of formula vii) or x) and R¹ and R⁵ represent hydrogen atoms.

3. The gel according to claim 1, wherein the compound of formula (I) is (II)

wherein R² and R³ are independently of each other —H or —OH.

4. The gel according to claim 1, wherein the compound of formula (I) is guanosine-5'-hydrazide.

5. The gel according to claim 1, wherein the salt is of formula $M_yX_m$, wherein X is an anion selected from the group consisting of Cl⁻, NO₃⁻, HCOO⁻, CH₃COO⁻HCO₃⁻, H₂PO₃⁻, HPO₃²⁻, SO₄²⁻ CO₃²⁻, PO₃³⁻ and citrate³⁻, M is a cation selected from the group consisting of Na⁺, K⁺, Sr²⁺, NH₄+ or (CH₃)₄N+, and y and m are individually selected to be 1, 2 or 3 in to give a neutral total charge for the salts of formula $M_yX_m$.

6. The gel according to claim 1, wherein the water-based liquid is water or an homogeneous mixture of water with ethanol, dipropylene glycol or propylene glycol.

7. The gel according to claim 1, wherein the water-based liquid has a pH comprised between 5 and 8.

8. An active gel comprising a mixture of:
at least one active substance, and
a gel, as defined in claim 1.

9. The active gel according to claim 8, wherein the active substance is a perfuming ingredient.

10. A consumer article comprising a gel according to claim 8.

11. The consumer article according to claim 10, in a form selected from the group consisting of a perfuming or sanitizing device, a diaper pail freshener, a car freshener, a closet freshener, a cat litter box freshener, a shoe freshener or a garbage pail freshener, a toothpaste, a cosmetic or pharmaceutical cream, a hair care or body care product, a cleaning product, a surface polishing article, an insecticide or an insect attractant or repellent device.

12. A method of delivering at least one active substance selected from the group consisting of a flavoring ingredient, a perfuming ingredient, a pharmaceutical ingredient, an insect attractant or repellent or an agrochemical wherein the method comprises combining the active substance with an effective amount of a gel composition according to claim 8 to protect the at least one active substance from degradation and to facilitate delivery in a controlled manner to the environment.

13. A compound of formula

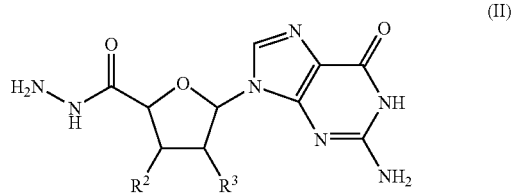

(II)

wherein $R^2$ and $R^3$ are independently of each other —H or —OH.

14. The compound of claim 13 specifically as guanosine-5'-hydrazide.

15. A gel comprising the compound of claim 14.

16. A consumer article comprising a gel according to claim 15.

17. The consumer article according to claim 16, in a form selected from the group consisting of a perfuming or sanitizing device, a diaper pail freshener, a car freshener, a closet freshener, a cat litter box freshener, a shoe freshener or a garbage pail freshener, a toothpaste, a cosmetic or pharmaceutical cream, a hair care or body care product, a cleaning product, a surface polishing article, an insecticide or an insect attractant or repellent device.

18. A method of delivering at least one active substance selected from the group consisting of a flavoring ingredient, a perfuming ingredient, a pharmaceutical ingredient, an insect attractant or repellent or an agrochemical wherein the method comprises combining the active substance with an effective amount of a gel composition according to claim 15 to protect the at least one active substance from degradation and to facilitate delivery in a controlled manner to the environment.

* * * * *

UNITED STATES PATENT AND TRADEMARK OFFICE
CERTIFICATE OF CORRECTION

| | |
|---|---|
| PATENT NO. | : 7,981,436 B2 |
| APPLICATION NO. | : 11/851106 |
| DATED | : July 19, 2011 |
| INVENTOR(S) | : Lehn et al. |

It is certified that error appears in the above-identified patent and that said Letters Patent is hereby corrected as shown below:

Column 26:
Line 12, change "$R^5$is" to --$R^5$ is--.
Line 18, change "$NH_4^+$or" to --$NH_4^+$ or--.
Line 21, change "picrate⁻and" to --picrate⁻ and--.
Line 44, change "guanosine-5 '-hydrazide." to --guanosine-5'-hydrazide.--.
Line 47, change "$CH_3COO^-HCO_3^-$," to --$CH_3COO^-$, $HCO_3^-$,--.
Line 50, change "$NH_{4+}$ or $(CH_3)_4N+$," to --$NH_4^+$ or $(CH_3)_4N^+$,--.

Signed and Sealed this
Thirtieth Day of August, 2011

David J. Kappos
*Director of the United States Patent and Trademark Office*